United States Patent [19]

Alexandrov et al.

[11] Patent Number: 4,960,516

[45] Date of Patent: Oct. 2, 1990

[54] LIQUID MICROCOLUMN CHROMATOGRAPH

[76] Inventors: Maxim L. Alexandrov, prospekt Engelsa, 63, korpus 3, kv. 89; Boris G. Belenky, Liteiny prospekt, 46, kv. 10; Vladimir A. Gotlib, Vasilievsky ostrov, 4 linia, 1/3, kv. 65; Arkady P. Vlasov, ulitsa Beringa, 32 korpus 1, kv. 11; Nikolai N. Komarov, ulitsa Trefoleva, 6/30, kv. 64; Valery V. Sudiiin, Lakhtinskaya ulitsa, 20, kv. 14; Vsevolod V. Shevkunov, ulitsa Stakhanovtsev, 12, kv. 34, all of Leningrad, U.S.S.R.

[21] Appl. No.: 328,034

[22] PCT Filed: Jun. 16, 1987

[86] PCT No.: PCT/SU87/00068

§ 371 Date: Jan. 23, 1989

§ 102(e) Date: Jan. 23, 1989

[87] PCT Pub. No.: WO88/10425

PCT Pub. Date: Dec. 29, 1988

[51] Int. Cl.⁵ .............................................. B01D 15/08
[52] U.S. Cl. .................................. 210/198.2; 210/101; 210/137; 422/70
[58] Field of Search ...................... 210/101, 137, 198.2; 55/386; 422/70

[56] References Cited

U.S. PATENT DOCUMENTS 4,165,284 8/1979 Guillemin et al. ............... 210/198.2
4,234,427 11/1980 Boehme ........................... 210/198.2

FOREIGN PATENT DOCUMENTS 54-19194 7/1979 Japan ................................. 210/198.2
715996 2/1980 U.S.S.R. ........................... 210/198.2
1092410 5/1984 U.S.S.R. ........................... 210/198.2

Primary Examiner—Ernest G. Therkorn
Attorney, Agent, or Firm—Ladas & Parry

[57] ABSTRACT

The liquid microcolumn chromatograph comprises a microcolumn (1), unit (2) for feeding eluent, made as a reservoir (3) separated by a "slack" diaphragm (4) into two half-chambers (5,6) one whereof communicates with a source (7) of pressure and the other is connected to a source (8) of eluent and to an inlet into the microcolumn (1) a flow-through cell (9), and an eluent-collecting vessel (14). The chromatograph is provided with an additional reservoir (10) separated by a "slack" diaphragm (11) into two half-chambers (12, 13) and is also provided with an additional source (15) of pressure, the half-chamber (12) being communicated with an outlet of the flow-through cell (9) and connected to the eluent-collecting vessel (14), whereas the half-chamber (13) communicates with the additional source (15) of pressure.

4 Claims, 1 Drawing Sheet

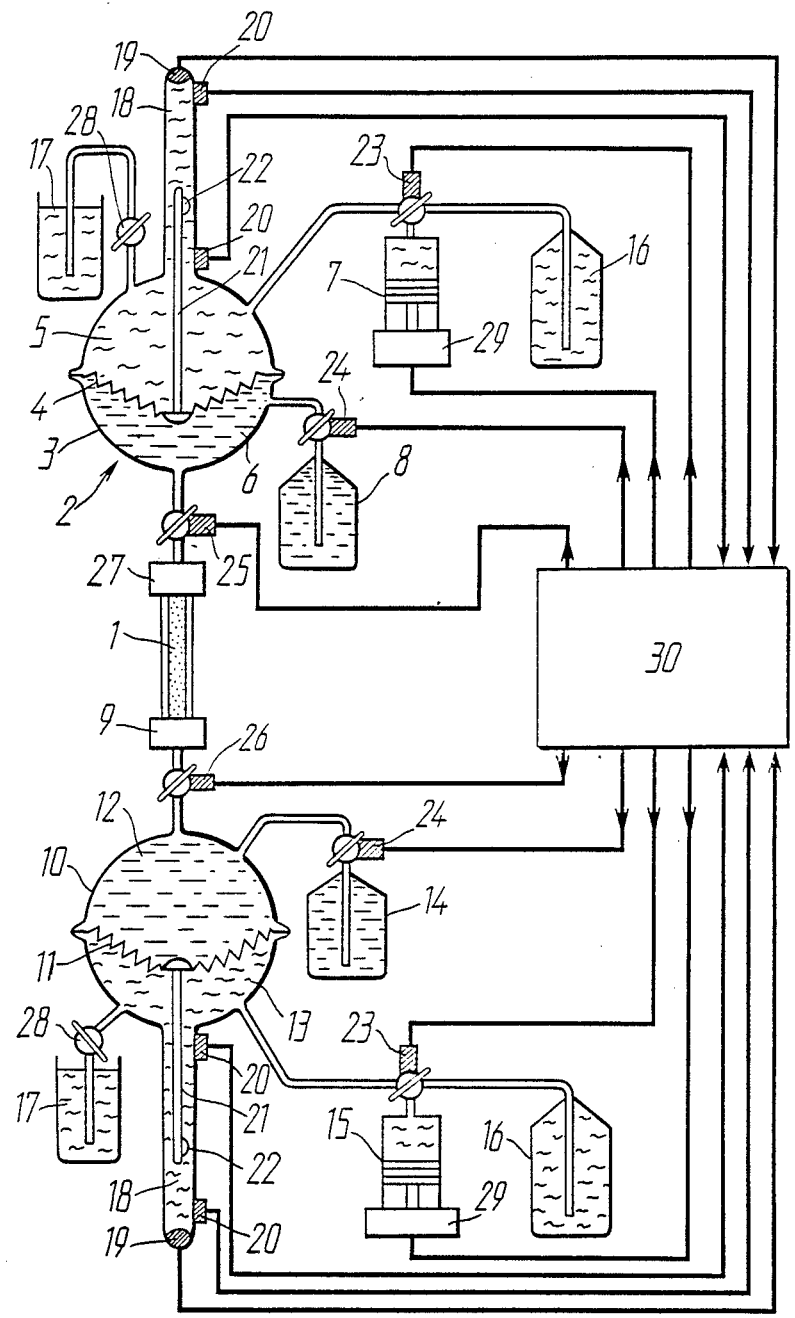

LIQUID MICROCOLUMN CHROMATOGRAPH

FIELD OF THE ART

The present invention relates to analytical instrumentation and has specific reference to the design of liquid microcolumn chromatographs.

PRIOR ART

Known in the art is a liquid microcolumn chromatograph comprising a microcolumn, a unit for feeding eluent in the form of a reservoir separated by a "slack" diaphragm into two chambers of which one communicates with a source of pressure and is filled with a working agent and the other chamber communicates with a source of eluent and with an inlet into the microcolumn, a flow-through cell of a detector located at the outlet of the microcolumn, and an eluent receiver (SU, A, 715996).

In microcolumn chromatography columns with sorbent are used, the particle size of the sorbent being on the order of units of microns. The pressure gradient in such columns reaches hundreds of atmospheres. A high pressure gradient in the microcolumn makes the etuent flow through the heterogenous packing of the column non-uniform. High pressure surges set up when the components of the sample are passing through the sorbent of the microcolumn fail to coincide with the time of passage of these components through the detector cell. Consequently, the detector (which is commonly a high-sensitive one of the refractometer type) records blurred boundaries of chromatographic peaks, corresponding to each component, i.e. the shape of the peaks fails to represent the actual composition of the sample. Moreover, bubbles of the solute gas liberated from the eluent due to the sharp drop in pressure brought about by the descent of the eluent down the chromotographic microcolumn on the one hand, block sorbent channels and, on the other hand, are recorded pores by the detector and interfere with the useful signal. As a result, the accuracy of chromatographic analysis is impaired.

To eliminate the above-stated disadvantages in liquid chromatographs, it is known to employ a means of setting up a backpressure at the outlet of the chromatographic column. Thus, a liquid chromatograph is known, wherein the backpressure at the column outlet is provided in the form of a liquid column (JP, B, 54-19194).

However, the known means of providing backpressure cannot be used in conjunction with liquid microcolumn chromatographs which require that the outlet pressure in the microcolumn should be of the same order as the inlet one-commonly of a significant value as already mentioned above. Only on condition that this requirement is met the pressure fluctuations in the microcolumn can amount to fractions of percent of the pressure in the cell of the detector. To make a liquid column capable of ensuring a requisite outlet pressure in a microcolumn is not feasible.

DISCLOSURE OF THE INVENTION

It is an object of the invention to provide a liquid microcolumn chromatograph which would be equipped with a means for setting up a backpressure at the outlet of the microcolumn thereof, featuring a simple and reliable design, which would enable the elimination of evolution of gas bubbles at the microcolumn outlet, as well as fluctuations of pressure in the microcolumn and, in the final run, enable an increase in the confidence and accuracy of chromatographic analysis.

The essence of the invention consists in that a liquid microcolumn chromatograph comprising a microcolumn, a unit for feeding eluent designed as a main reservoir separated by a "slack" diaphragm into two half-chambers of which one communicates with a main source of pressure and is filled with a working agent and the other half chamber communicates with a source of eluent and with an inlet to the microcolumn, a flow through cell of a detector at the microcolumn outlet, and an eluent receiver, according to the invention, is provided with an additional reservoir separated by a "slack" diaphragm into two half-chambers and given a volume which is essentially greater than the volume of the eluent needed for one analysis and is also provided with an additional source of pressure, one half-chamber of the additional reservoir communicating with an outlet of the flow-through cell of the detector and with the eluent receiver and the other half-chamber of the additional reservoir communicates with the additional source of pressure.

It is expedient that the main and additional reservoirs should be identical in design, the inside surfaces of their half-chambers be shaped each as a body of revolution, and the surface area of the "slack" diaphragm be equal to or greater than the area of the inside surface of the half chamber.

It is also expedient that a pickup of the position of the "slack" diaphragm be provided in each of the half-chambers communicating with the corresponding source of pressure.

The pickup of the position of the "slack" diaphragm may be made in the form of a cylindrical hollow projection on the surface of the half-chamber, which is fitted with signalling elements indicating the two extreme positions of the "slack" diaphragm and contains a rod attached to the centre of the "slack" diaphragm with one rod end carrying a signalling element indicating a current position of the "slack" diaphragm at the other end, the rod being installed with a possibility of moving inside the projection and interacting by the signalling element thereof with the signalling elements of the projection.

At the outlet of the flow-through cell of the detector in the liquid microcolumn chromatograph according to the invention there is located a means of setting up a backpressure at the outlet of the flow-through cell of the detector which is of a value commensurable with the value of the pressure at the inlet to the chromatographic column. Owing to this backpressure, the pressure surges resulting from the passage of sample components through the sorbent of the microcolumn are negligibly small and no gas bubbles are formed at the outlet from the column. Apart from that, any pressure surges which are set up are snubbed owing to the presence of the additional voluminous reservoir at the outlet from the flow-through cell. Since all the eluent needed for analyzing thousands of samples is contained between the two "slack" diaphragms which interact with the working fluid found under the same pressure all pressure surges arising in the hydraulic system of the chromatograph—such as those due to the jerkwise feeding of the eluent by step motor-actuated syringe pumps, operation of a sample-feeding stopcock and other automatic stopcocks—are snubbed. As a result, any possibility of generating spurious signals, distorting the shape of chromographic peaks and that of detector background is eliminated, the accuracy and sensitivity of the detector are increased.

BRIEF DESCRIPTION OF THE DRAWING

The sole figure shows a general schematic view of the liquid microcolumn chromatograph according to the invention.

DESCRIPTION OF THE PREFERRED EMBODIMENTS

Referring to the drawing, the liquid microcolumn chromatograph comprises a microcolumn 1 packed with a fine sorbent, a unit 2 for feeding eluent which is provided in the form of a reservoir 3 separated by a "slack" diaphgragm 4 into two half-chambers 5 and 6, whereby the half-chamber 5 communicates with a source 7 of pressure—e.g. a syringe pump—and is filled with a working agent and the half chamber 6 communicates with a source 8 of eluent and with an inlet to the microcolumn 1. Connected to an outlet from the microcolumn 1 is a flow-through cell 9 of a highly sensitive laser detector (not shown), which is also connected to an additional reservoir 10 the volume whereof is essentially greater than that of the eluent needed for one analysis. The additional reservoir 10 is separated by a "slack" diaphragm 11 into two half-chambers 12 and 13, whereby the half-chamber 12 communicates with the flowthrough cell 9 and with an eluent-collecting vessel (receiver) 14 and the half-chamber 13 communicates with an additional source 15 of pressure (e.g. a syringe pump or a cylinder with gas). The half-chamber 13 is filled with a working agent (an inert incompressible lubricating liquid or a gas). The sources 7, 15 of pressure, provided they are syringe pumps (as shown in the drawing), are connected each to an auxiliary reservoir 16 containing the working agent which is used to refill the delivery ends of the pumps after delivery strokes for injecting pressurized liquid. Precision syringe pumps feature ultrasmall deliveries (units of microlitres per minute per stroke) and cannot have voluminous delivery ends. Therefore their their regular refilling is indispensable.

The working agent-filled half-chambers 5, 13 are provided each with a drain vessel 17 usable during the adjustments of the diaphragms 4, 11 for position in the reservoirs 3, 10. The half-chambers 5, 13 with the working agent and the half-chambers 6, 12 with the eluent are shaped as bodies of revolution, and the surface area of the "slack" diaphragms 4, 11 equals or is greater than the area of the inside surface of each of the half-chambers 5, 6, 12 and 13.

The half-chambers 5, 13 with the working agent are provided each with a hollow cylindrical projection 18 on their outside surface, the projection 18 being provided with a pressure transducer 19. Each projection 18 is provided with two signalling elements 20 serving to monitor the two extreme positions of the "slack" diaphragms 4, 11 inside the reservoirs 3, 10. Two rods 21 capable of moving freely in the cylindrical projections 18 are linked each to the centres of the corresponding "slack" diaphragms 4 and 11. At the opposite end of each rod 21 a signalling element 22 is provided which generates a signal in the element 20 at the instant the element 22 is located opposite the element 20. A remotely-operated stopcock 23 is provided at the delivery end of each of the sources 7, 15 of pressure. Similar remotely-operated stopcocks 24 are provided at the eluent-containing reservoirs 8, 14, and remotely-operated stopcocks 25, 26 are provided at the inlet to and at the outlet from the chromatographic column 1, respectively. The stopcock 25 is located upstream of a metering means 27 which is secured directly to the inlet end face of the microcolumn 1, and the stopcock 26 is located downstream of the flow-through cell 9 which is also secured directly to the outlet end face of the microcolumn 1.

Hand-operated stopcocks 28 which can be set either "open" or "closed" are provided on the lines connecting the chambers 5, 13 with the drain vessels 17.

The pressure trensducers 19, the signalling elements 20, an electric drive 29 of the sources 7, 15 of pressure and the actuators of the remotely-operated stopcocks 23, 24, 25, 26 are connected to a control computer 20.

The liquid microcolumn chromatograph operates as follows. The half-chamber 6 of the unit 2 for feeding eluent is refilled with a fresh eluent and the half-chamber 12 of the additional reservoir 10 is drained of the eluent spent during the preceding analyses, obeying the signals of the computer 30.

The motive force for the operations of redistributing liquids in the chromatograph is provided by the sources 7, 15 of pressure exerting their action on the inert working agent in the half-chambers 5 and 13. A discharge of the working agent from the half-chambers 5, 13 initiates the refilling of the chambers 6, 14 with the eluent from the vessels 8, 14, provided the stopcocks 24 have been set open by a signal from the computer 30. The eluent contained in the half-chambers 5, 12 is admitted into the chromatographic column 1 owing to the delivery of the working agent either into the half-chamber 5 or the half-chamber 13, depending on the direction of admitting the eluent. The pressure sustained by the working agent is applied to the eluent by way of either the diaphragm 4 or the diaphragm 11, and the rate of feeding the working agent equals the rate of pumping the eluent through the packing of the microcolumn 1. Drained of the eluent is that of the half-chambers 6, 12 which is exposed to a higher pressure, the other half-chamber being filled at the same time. To that end, the syringe pumps (the sources 7, 15 of pressure) must operate in antiphase. The pump ensuring a higher pressure must be on a delivery stroke, while the pump at the opposite end of the microcolumn 1 must be on a suction stroke (the plunger would move downwards).

Since the delivery ends of the syringe pumps have a small volume, a number of refilling-draining cycles of the delivery end of the source 7 of pressure are required before the half-chamber 6 is filled with the eluent in an amount sufficient for carrying out several thousands of analyses of the chromatograph.

Concurrently with the above operations, the delivery end of the source 15 of pressure is refilled with the working agent in order to have this agent in stock in an amount required for expelling the spent eluent from the half-chamber 12 into the eluent-collecting vessel 14.

The procedure of stocking the chromatograph with fresh eluent is as follows. The stopcocks 25, 26, 28 are closed and the stopcocks 24 are opened. The source 7 of pressure (syringe pump) begins a suction stroke (the pluger moves downwards) so that the working agent contained in the half-chamber 5 enters the delivery end of the pump. The line connecting the delivery end of the pump to the auxiliary reservoir 16 is closed by the stopcock 23. As soon as the delivery end of the pump is filled with the working agent, a signal from the computer 30 causes the stopcock 23 to open the line connecting the pump to the auxiliary reservoir 16 and to close the line from the pump to the half-chamber 5. Another signal of the computer 30 sets the electric drive 29 of the pump into operation which ejects the liquid from the delivery end into the auxiliary reservoir 16. When the stopcock 23 connects the delivery end of the pump to the half-chamber 5, the pump draws another portion of the working agent from the half-chamber 5. During these cycles similar amounts of the fresh eluent contained in the source 8 of eluent are drawn into the half-chamber 6.

The position of the diaphragm 4 indicative of the amounts of the working agent and eluent in the half-chambers 5 and 6, respectively, is monitored by the signalling elements 20 when they are passed by the signalling element 22 attached to the rod 21. The rod 21 reciprocates freely within the cylindrical projection 18 being acted upon by the diaphragm 4 it is linked to. When the bulk of the working agent has been drawn from the half-chamber 5 and the rod 21 has entered the interior of the projection 18 so that the signalling element 22 at the end of the rod 21 registers with the signalling element 20 of the projection 18, the pump (i.e. the source 7 of pressure) is automatically stopped by the computer 30. The reservoir 3 is then filled with eluent in an amount significantly exceeding (thousand-fold) the quantity needed for a single analysis.

Likewise, the half-chamber 12 of the additional reservoir 10 is being drained, provided the stopcocks 25, 26, 28 are closed while the stopcock 24 is open. The eluent accumulated in the half-chamber 12 is expelled by the diaphragm 11 into the eluent-collecting vessel 14, whereas the source 15 of pressure delivers the working agent into the half-chamber 13. The delivery end of the syringe pump, if one is being used, is filled with the working agent from the auxiliary reservoir 16 during the back stroke of the pump, provided the stopcock 23 is set so as to connect the delivery end of the pump to the auxiliary reservoir 16 and the line connecting the pump end to the half-chamber 13 is closed. The signal indicative of the extreme positions of the diaphgragm 11 comes from the signalling elements 20 in the same way as this was described referring to the diaphragm 4. At the end of draining the reservoir 10, this becomes filled with the working agent and the spent eluent is accumulated in the eluent-collecting vessel 14. In response to signals of the computer 30, the stopcocks 25, 26 protecting the microcolumn 1 are opened, the stopcocks 24 are closed and the stopcocks 23 are set so as connect the filled delivery ends of the pumps (the sources 7, 15 of pressure) to the half-chambers 5 and 13. The source 7 of pressure induces a flow of eluent through the column 1 and the source 15 of pressure sets up a backpressure at the outlet from the column 1 which is of a value providing for a given outlet-to-inlet pressure ratio. The pressure transducers 19 provided in the cylindrical projections 18 measure the inlet and outlet pressures in the column 1. As soon as the given values of these pressures (say 200 or 100 atm) are attained, a sample is introduced into the column 1 with the aid of the metering means 27. The separation process takes then place, and the separated solutes are detected and measured while passing through the chromotank 9. The microcolumn 1 is rinsed by circulating fresh eluent therethrough, and the next sample is injected. The draining vessels 17 with the stopcocks 28 are used for adjusting the chromatograph, e.g. for equalizing the positions of the diaphragms 4, 11 in the reservoirs 3, 10 or for draining some working agent when the source 15 of pressure is a cylinder with gas.

If the sources 7, 15 of pressure are identical syringe pumps, these must operate in antiphase. This means that at the time one of the pumps is on a delivery stroke, injecting eluent into the column 1, the other pump must be on a suction stroke at the same speed (provided the given backpressure has been set up during the preparation of the system).

More often than not working agent is delivered in small amounts and is regularly drained into the draining (vessel 17). The detector background is noted every time.

A salient feature of the herein-proposed liquid microcolumn chromatograph is that the microcolumn 1 is connected at both ends to the reservoirs 3, 10 the volume whereof is tenths thousands times greater than the free volume of the microcolumn 1. Moreover, the reservoirs 3, 10 are always filled with liquids sustaining high pressure. Compared with this pressure, the pressure surges resulting from the operation of the step motors of the electric pump drives 29 or from the elution of a sample through the microcolumn 1 amount to small fractions of percent. The large volumes of liquids snub the pressure surges. A delivery of a portion of liquid needed for a signal analysis from the unit 2 for feeding the eluent into the additional reservoir 10 changes the pressure in this last-named reservoir only by about 0.01%, i.e. by an amount which is outside the range of detector sensitivity.

Also on the positive side of the chromatograph according to the invention is the equalization of the temperature of the eluent before and after the microcolumn 1. In other words, no difference exists between the temperature of the cell 9 and that of the eluent which is a factor of importance if use is made of refractometers. Large volumes of liquids before and after the microcolumn 1 cannot have an appreciable temperature gradient. Therefore an adequate thermal stability is provided to obtain accurate measurements. To that end it is good practice to make both reservoirs 3, 10 of a material displaying good thermal conductivity and link them by structural elements of the same kind which would also surround the microcolumn 1 and the flow-through cell 9. Most of the chromatographs meet this requirement and their microcolumn 1 is either in metal or is provided with a metal casing.

The present liquid microcolumn chromatograph finds in the analysis of complex mixtures of organic compounds when the sample for the test in question is too small for a conventional treatment. This may be the case, for example, in medicine in connection with analyzing smears taken from organs of recently born babies. Likewise, in genetic engineering a need may arise to determine the structure of hormones and enzymes, both synthetic and produced in the body. Determining the amount of pesticides in insects is a problem confronted with in agriculture. Criminology resorts to liquid microcolumn chromatography and so do various domains of science and engineering.

What is claimed is:

1. A liquid microcolumn chromatograph comprising a microcolumn (1), a unit (2) for feeding eluent, said unit being made as a main reservoir (3) separated by a "slack" diaphragm (4) into two half-chambers (5, 6) of which one communicates with a main source (7) of pressure and is filled with a working agent, while the other is connected to a source (8) of eluent and to an inlet to the microcolumn (1), a flow-through cell (9) of a detector at the outlet of the microcolumn (1), and an eluent-collecting vessel (14), c h a r a c t e r i z e d in that it is provided with an additional vessel (10) whose volume is essentially greater than that of the eluent required for carrying out a single analysis, separated by a "slack" diaphragm (11) into two half-chambers (12, 13), and with an additional source (15) of pressure, the half-chamber (12) communicating with the outlet of the flow-through cell (9) of the detector and with the eluent-collecting vessel (14), whereas the half-chamber (13) is communicated with an additional source (15) of pressure.

2. A liquid microcolumn chromatograph according to claim 1, c h a r a c t e r i z e d in that the main and additional reservoirs (3, 10) are identical and the inner surface of the half-chambers (5, 6, 12, 13) thereof is a body of revolution, whereas the surface area of the "slack" diaphragm (4, 11) is equal to or greater than the area of the inner surface of the half-chamber (5, 6, 12, 13).

3. A microcolumn chromatograph according to claim 1 or 2, c h a r a c t e r i z e d in that in each half-chamber (5, 13), communicated with its source (7, 15) of pressure, a pickup of the position of the "slack" diaphragm (4, 11) is arranged.

4. A microcolumn chromatograph according to claim 3, c h a r a c t e r i z e d in that the pickup of the position of the "slack" diaphragm (4, 11) is made as a hollow cylindrical projection on the surface of the half-chamber (5, 13) and is equipped with signalling elements (20) monitoring two extreme positions of the "slack" diaphragm (4, 11), and a rod (21) whose one end is linked with the centre of the "slack" membrane (4, 11) and whose other end carries a signalling element (22) indicating a current position of the "slack" diaphragm (4, 11), said rod being movable within the projection (18) and interacting by its signalling element (22) with the signalling elements (20) of the projection 18.

* * * * *